(12) United States Patent
Schönhammer

(10) Patent No.: US 9,155,696 B2
(45) Date of Patent: Oct. 13, 2015

(54) PHARMACEUTICAL COMPOSITIONS

(75) Inventor: Karin Schönhammer, Basel (CH)

(73) Assignee: Novartis AG, Basel (CH)

( * ) Notice: Subject to any disclaimer, the term of this patent is extended or adjusted under 35 U.S.C. 154(b) by 922 days.

(21) Appl. No.: 13/058,074

(22) PCT Filed: Aug. 11, 2009

(86) PCT No.: PCT/EP2009/060366
§ 371 (c)(1),
(2), (4) Date: Mar. 10, 2011

(87) PCT Pub. No.: WO2010/018159
PCT Pub. Date: Feb. 18, 2010

(65) Prior Publication Data
US 2011/0183905 A1 Jul. 28, 2011

(30) Foreign Application Priority Data

Aug. 12, 2008 (EP) .................................... 08162213
Oct. 1, 2008 (EP) .................................... 08165662
Feb. 3, 2009 (EP) .................................... 09151917

(51) Int. Cl.
| | |
|---|---|
| *A61K 38/12* | (2006.01) |
| *A61K 9/00* | (2006.01) |
| *A61K 38/31* | (2006.01) |
| *A61K 47/10* | (2006.01) |
| *A61K 47/34* | (2006.01) |

(52) U.S. Cl.
CPC ................. *A61K 9/0024* (2013.01); *A61K 9/00* (2013.01); *A61K 38/12* (2013.01); *A61K 38/31* (2013.01); *A61K 47/10* (2013.01); *A61K 47/34* (2013.01)

(58) Field of Classification Search
CPC ........ A61K 9/0024; A61K 9/00; A61K 38/12
USPC .................. 530/317; 514/11.1, 21.1; 424/486
See application file for complete search history.

(56) References Cited

U.S. PATENT DOCUMENTS

| | | |
|---|---|---|
| 2003/0082234 A1 | 5/2003 | Seo et al. |
| 2008/0213330 A1 | 9/2008 | Lambert |

FOREIGN PATENT DOCUMENTS

| | | |
|---|---|---|
| WO | WO 99/21908 | 5/1999 |
| WO | WO 01/45742 | 6/2001 |
| WO | WO 02/45689 | 6/2002 |
| WO | WO 03/045351 | 6/2003 |
| WO | WO 2005/120453 | 12/2005 |
| WO | WO 2006/017852 | 2/2006 |
| WO | 2007075480 A2 | 7/2007 |

OTHER PUBLICATIONS

Schoenhammer K. et al. "Injectable in situ forming depot systems: PEG-DAE as novel solvent for improved PLGA storage stability", International Journal of Pharmaceutics, vol. 371, pp. 33-39, 2008.

*Primary Examiner* — David Lukton
(74) *Attorney, Agent, or Firm* — Michelle Han

(57) ABSTRACT

A liquid pharmaceutical composition comprising a biodegradable polymer, polyethylene glycol having a molecular weight of less than 600 Daltons, a pharmaceutically active agent and less than 0.5% of an biologically acceptable organic solvent.

14 Claims, 8 Drawing Sheets

PHARMACEUTICAL COMPOSITIONS

This Application is a 371 of International Application No. PCT/EP2009/060366 filed on Aug. 11, 2011, which claims benefit of EP Application 08162213.6 filed on Aug. 12, 2008, EP Application 081656621.1 filed on Oct. 1, 2008, and EP Application 09151917.3 filed on Feb. 3, 2009, the entire disclosures of which are hereby incorporated by reference.

The present invention relates pharmaceutical compositions, more specifically to injectable in situ forming depot formulations comprising a pharmaceutically active agent and to a process for preparing said depot formulations.

In-situ forming depots represent a specific class of polymeric delivery systems with the advantages of a straightforward manufacturing even for sensitive molecules and ease of application since the polymer solidifies after application by phase separation. When based on a biodegradable polymer like the frequently used poly (D,L lactide-co-glycolide)s (PLGA), the depot degrades over the time. Currently, there are two injectable in-situ forming depots on the market: Atridox® and Eligard®. Both products were developed on Atrigel's technology by Dunn et al. (H. B. Ravivarapu, K. L. Moyer, R. L. Dunn, International Journal of Pharmaceutics, 194 (2000) 181-191) comprising PLGA dissolved in 1-methyl-2-pyrrolidinone (NMP), a water miscible solvent and a drug substance powder to suspend in the solution prior to application.

Whereas injectable in-situ forming depots is an attractive, it is at the same time also a challenging application system. Besides chemical compatibility, local tolerability and acute toxicity, an important factor for an injectable in-situ forming depot is its storage stability as a liquid.

The present invention now provides in situ forming depot pharmaceutical formulations with improved characteristics with respect to tolerability and acute toxicity as well as storage stability and which are convenient to use, and which are particularly suitable for ready to use injectable depot formulations.

The present invention provides in one aspect an in situ forming depot pharmaceutical formulation comprising
(1) a hydrophobic or hydrophilic pharmaceutically active agent
(2) a biodegradable polymer,
(3) a biocompatible water miscible solvent which has a solidification point at a temperature between 8° to 20° C., preferably a poly (ethylene) glycol with a molecular weight 450<Mw<650 Da and with chemically inert end groups, preferably alkoxy endgroups, more preferred ethoxy and methoxy endgroups and optionally
(4) an additive.

The biocompatible water miscible solvent is preferably chosen among PEGs with a solidification point between 8° to 20° C., preferably between 10° to 16° C. to obtain a stable solid formulation at low temperature to avoid sedimentation of drug substance particles. In one embodiment the solidification point is <15° C. The PEG used as solvent has inert end groups to obtain improved stability as well as lower viscosity compared to non end-capped PEGs of same molecular weight. In a preferred embodiment, polyethylene glycol mono and di-alkyl ether such as e.g. dimethylether or diethylether PEGs are used. In a another preferred embodiment, the molecular weight of the end-capped PEG is between 500 and 600 Da, in a more preferred embodiment the Mw is 450, 500, 550 or 650 Da. In a particularly preferred embodiment, the PEG is chosen from polyethylene glycol 500 dimethylether (also known as PEG500DME or PEG DME 500 or PEG 500 DME and commercially available e.g. from Clariant Glymes, melting temperature ca. 13° C.). The terms "solidification point" and "melting point" are interchangeable as used herein. Determination of melting/solidification temperature is within the skill of the ordinary artisan and can e.g. be performed using DSC. The PEGs of the present invention show low hemolysis and toxicity potential.

The pharmaceutical compositions of the present invention are in a solid state at storage temperatures of 2-8° C. (typical refrigerator temperature) and are liquid and free or substantially free from sedimentation at room temperature. The pharmaceutical compositions (without drug substance) of the present invention have a viscosity suitable for an easy injection, e.g. injectable s.c. or i.m., when equilibrated to room temperature. The dynamic viscosity of the polymer solution (pharmaceutical composition without drug substance) is preferably between 300 and 800 mPas. The pharmaceutical compositions of the present invention are particularly useful for ready to use devices because no re-suspending step is required prior to application.

The pharmaceutically active agent may be dissolved or dispersed in liquid polyethylene glycols (PEG) with modified end groups as described above e.g. polyethylene glycol mono (USP 31 NF26) and di-alkyl ether e.g. at room temperature (e.g. 25° C.), e.g. depending on its solubility in this solvent with or without a co-solvent. In a preferred embodiment no co-solvent, such as e.g. an organic solvent, is used.

The pharmaceutically active agent (also interchangeably called drug substance herein) can be a hydrophilic or hydrophobic, small organic molecule, peptide or protein. The pharmaceutically active agent can be in form of the free base, free acid or a salt.

Examples of pharmaceutically active agents include but are not limited to peptides, polypeptides, proteins, carbohydrates, oligonucleotides, RNA and DNA. A few examples of peptides are antibodies, growth hormones, e.g. epidermal growth factor (EGF), prolactin, luliberin or luteinizing hormone releasing hormone (LH-RH), glucagon, gastrin, pentagastrin, urogastron, secretin, enkephalins, endorphins, angiotensins, renin, bradykinin, bacitracins, polymyxins, colistins, tyrocidin, gramicidines, insulin, interferons, erythropoietin, calcitonin, heparin, somatostatin analogues, e.g. somatostatin pamoate or di-aspartate, cell stimulating factors and parathyroid hormones. Other examples include bisphosphonates such as e.g. pamidronic acid, alendronic acid, ibandronic acid, risedronic acid, zoledronic acid, GnRH agonists and analogues such as e.g. leuprorelide acetate, triptorelin acetate or pamoate, buserelin, histrelin acetate or hormone contraceptives such as etonogestrel, levonogestrel. Further examples include minocycline, risperidone, naltrexone, carmustine.

A preferred active agent may be a somatostatin analogue. Somatostatin is a tetradecapeptide having the structure H-Ala-Gly-Cys-Lys-Asn-Phe-Phe-Trp-Lys-Thr-Phe-Thr-Ser-Cys-OH
 1   2   3   4   5   6   7   8   9  10  11  12  13  14

(with a disulfide bridge between Cys-3 and Cys-14)

Somatostatin analogues of particular interest include octreotide, e.g. as disclosed in U.S. Pat. No. 4,395,403, lanreotide or pasireotide. Somatostatin analogues of particular interest have also been described e.g. in WO97/01579 and WO02/010192. Said somatostatin analogues comprise the amino acid sequence of formula I

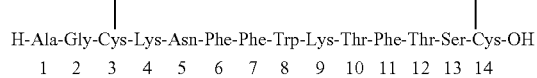

-(D/L)Trp-Lys-X$_1$-X$_2$-    I wherein $X_1$ is a radical of formula (a) or (b)

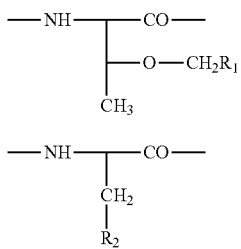

wherein $R_1$ is optionally substituted phenyl, wherein the substituent may be halogen, methyl, ethyl, methoxy or ethoxy, $R_2$ is —$Z_1$—$CH_2$—$R_1$, —$CH_2$—CO—O—$CH_2$—$R_1$,

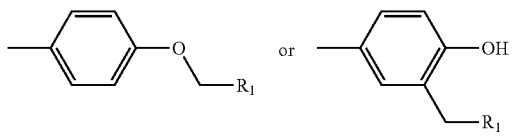

wherein $Z_1$ is O or S, and
$X_2$ is an α-amino acid having an aromatic residue on the $C_\alpha$ side chain, or an amino acid unit selected from Dab, Dpr, Dpm, His, (Bzl)HyPro, thienyl-Ala, cyclohexyl-Ala and t-butyl-Ala, the residue Lys of said sequence corresponding to the residue $Lys^9$ of the native somato-statin-14.

By somatostatin analogue as used herein is meant a straight-chain or cyclic peptide derived from that of the naturally occurring somatostatin-14, comprising the sequence of formula I and wherein additionally one or more amino acid units have been omitted and/or replaced by one or more other amino acid radical(s) and/or wherein one or more functional groups have been replaced by one or more other functional groups and/or one or more groups have been replaced by one or several other isosteric groups. In general the term covers all modified derivatives of the native somatostatin-14 comprising the above sequence of formula I which have binding affinity in the nM range to at least one somatostatin receptor subtype as defined hereinafter.

Preferably, the somatostatin analogue is a compound in which the residues at positions 8 through 11 of the somatostatin-14 are represented by the sequence of formula I as defined above.

Particularly preferred are compounds of formula III

II

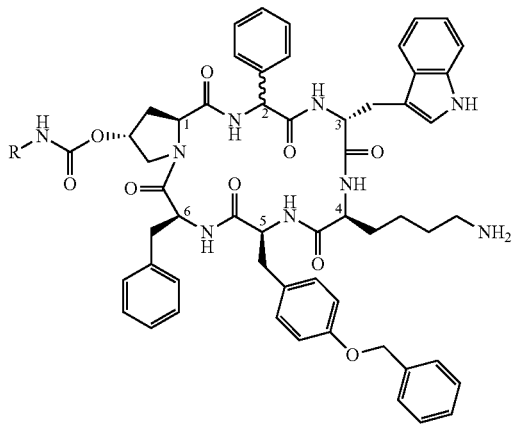

wherein the configuration at C-2 is (R) or (S) or a mixture thereof, and
wherein R is $NR_{10}R_{11}$—$C_{2-6}$alkylene or guanidine-$C_{2-6}$alkylene, and each of $R_{10}$ and $R_{11}$ independently is H or $C_{1-4}$alkyl,
in free form, in salt form or protected form.

Preferably R is $NR_{10}R_{11}$—$C_{2-6}$alkylene. Preferred compounds of formula II are the compounds wherein R is 2-amino-ethyl, namely cyclo[{4-($NH_2$—$C_2H_4$—NH—CO—O—)Pro}-Phg-DTrp-Lys-Tyr(4-Bzl)-Phe] (referred herein to as Compound A) and cyclo[{4-($NH_2$—$C_2H_4$—NH—CO—O—)Pro}-DPhg-DTrp-Lys-Tyr(4-Bzl)-Phe], in free form, salt form or protected form. Phg means —HN—CH($C_6H_5$)—CO— and Bzl means benzyl.

A compound of the invention may exist e.g. in free or salt form. Salts include acid addition salts with e.g. inorganic acids, polymeric acids or organic acids, for example with hydrochloric acid, acetic acid, lactic acid, aspartic acid, benzoic acid, succinic acid or pamoic acid. Acid addition salts may exist as mono- or divalent salts, e.g. depending whether 1 or 2 acid equivalents are added. Preferred salts are the lactate, aspartate, benzoate, succinate and pamoate including mono- and di-salts, more preferably the aspartate di-salt and the pamoate monosalt.

The polymer of the composition of the invention may be a synthetic or a natural polymer. The polymer may be either a biodegradable or a combination of biodegradable and non-biodegradable polymers, preferably a biodegradable polymer may be used. By "polymer" is meant a homopolymer or a copolymer.

As used herein, "biodegradable" means a material that should degrade by bodily processes to products readily disposable by the body and should not accumulate in the body.

Suitable polymers include
(a) linear or branched polyesters which are linear chains radiating from a polyol moiety, e.g. glucose,
(b) polyesters such as D-, L- or racemic polylactic acid, polyglycolic acid, polyhydroxybutyric acid, polycaprolactone, polyalkylene oxalate, polyalkylene glycol esters of acids of the Kreb's cycle, e.g. citric acid cycle, and the like and combinations thereof,
(c) polymers of organic ethers, anhydrides, amides, and orthoesters,
(d) copolymers of organic esters, ethers, anhydrides, amides, and orthoesters by themselves or in combination with other monomers.

The polymers may be cross-linked or non-cross-linked. Usually not more than 5%, typically less than 1% are cross-linked.

The preferred polymers of this invention are linear polyesters, and branched chain polyesters. The linear polyesters may be prepared from the α-hydroxy carboxylic acids, e.g. lactic acid and glycolic acid, by condensation of the lactone dimers, see e.g. U.S. Pat. No. 3,773,919, the contents of which are incorporated herein by reference. The preferred polyester chains in the linear or branched (star) polymers are copolymers of the α-carboxylic acid moieties, lactic acid and glycolic acid, or of the lactone dimers. The molar ratios of lactide:glycolide of polylactide-co-glycolides preferably used according to the invention is preferably from about 95:5 to 5:95, e.g. 75:25 to 25:75, e.g. 60:40 to 40:60, with from 55:45 to 45:55, e.g. 52:48 to 48:52, e.g. 50:50.

Linear polyesters, e.g. linear polylactide-co-glycolides (PLG), preferably used according to the invention have a weight average molecular weight (Mw) between about 1,000 and about 50,000 Da, e.g. about 10,000 Da, and a polydispersity $M_w/M_n$ e.g. between 1.2 and 2. The intrinsic viscosities of linear polymers of Mw 1000 to 50,000 are 0.05 to 0.6 dl/g, 0.1% in chloroform (at 25° C.) Suitable examples include e.g. those commonly known and commercially available as Resomers® from Boehringer Ingelheim, in particular Resomers® RG, e.g. Resomer® RG 502, 502H, 503, 503H.

Branched polyesters, e.g. branched polylactide-co-glycolides, preferably used according to the invention may be prepared using polyhydroxy compounds e.g. polyol e.g. glucose or mannitol as the initiator. These esters of a polyol are known and described e.g. in GB 2,145,422 B, the contents of which are incorporated herein by reference. The polyol contains at least 3 hydroxy groups and has a molecular weight of up to 20,000 Da, with at least 1, preferably at least 2, e.g. as a mean 3 of the hydroxy groups of the polyol being in the form of ester groups, which contain poly-lactide or co-poly-lactide chains. Typically 0.2% glucose is used to initiate polymerization. The branched polyesters (Glu-PLG) have a central glucose moiety having rays of linear polylactide chains, e.g. they have a star shaped structure.

The branched polyesters having a central glucose moiety having rays of linear polylactide-co-glycolide chains (Glu-PLG) may be prepared by reacting a polyol with a lactide and preferably also a glycolide at an elevated temperature in the presence of a catalyst, which makes a ring opening polymerization feasible.

The branched polyesters having a central glucose moiety having rays of linear polylactide-co-glycolide chains (Glu-PLG) preferably have a weight average molecular weight $M_w$ in the range of from about 1,000 to 55,000, preferably 20,000, e.g. 10,000 Da, and a polydispersity e.g. of from 1.1 to 3.0, e.g. 2.0 to 2.5. The intrinsic viscosities of star polymers of $M_w$ 10,000 to $M_w$ 50,000 are 0.05 to 0.6 dl/g in chloroform. A star polymer having a $M_w$ of 50,000 has a viscosity of 0.5 dl/g in chloroform.

The desired rate of degradation of polymers and the desired release profile for compounds of the invention may be varied depending on the kind of monomer, whether a homo- or a copolymer or whether a mixture of polymers is employed.

A mixture of polymers may comprise at least two different kinds of polymers, e.g. as listed under (a) to (e) above, or two polymers of the same polymer class with different properties. For example, a mixture of polymers may comprise a polymer having a medium weight average molecular, weight, e.g. from about 30,000 to about 50,000 Da, e.g. of about 20,000. Da, and of a polymer having a low weight average molecular weight, e.g. of about 2.000 to about 20,000 Da, e.g. of about 10,000 Da.

Preferably, the polymer matrix comprises a linear and/or branched polylactide-co-glycolide. More preferably, the polymer matrix comprises a Resomer® RG and/or a star polylactide-co-glycolide polymer having a weight average molecular weight of about 10,000 Da and/or a star polylactide-co-glycolide polymer having a weight average molecular weight of about 50,000 Da. The ratio of linear to branched polylactide-co-glycolide preferably is 0:100 to 100:0, e.g. 50:50 to 25:75 to 75:25.

In a particularly preferred embodiment the biodegradable polymer (e.g. PLA100 or PLGA50:50) has an inherent viscosity of 0.15-0.45 dL/g (0.1% in $CHCl_3$, 25° C.).

In another aspect the invention provides a process for preparing a injectable in situ forming depot formulation comprising the steps:
  (i) dissolving a biodegradable polymer, e.g. PLA or PLGA, in the solvent, e.g. an end-capped PEG with a solidification point between 8° to 20° C.,
  (ii) adding a pharmaceutically active agent and optionally an additive to achieve a solution or suspension, In case a suspension is obtained: continue with step iii)
  iii) DS particle size reduction by appropriate process, e.g. jet milling, ultrasound, high pressure homogenization, rotor-stator mixer (ultraturrax).

Alternatively, if the drug substance is soluble, steps (i) and (ii) can be switched.

The drug substance is dissolved or dispersed in the polymeric solution at a temperature where the solvent is liquid, conveniently e.g. room temperature. The dispersed drug substance may for instance be homogenized first by ultraturrax and then by ultrasound under cooling to expected particle size. A sterile product can be obtained by aseptic manufacturing or terminal sterilization.

This injectable in-situ depot shows an alternative controlled release formulation, easier in manufacturing and application than existing products. Compared to existing injectable in situ forming depots on polymer basis the depot formulation of the present invention is particularly useful as "ready to use devices" because with no re-suspending step is required prior to injection. The depot formulation of the present invention is the first formulation to be ready for injection after equilibration to room temperature. Dependant on viscosity the needle size can be adapted and drug load up to 10%, up to 7-5% or up to 5% as suspension is possible.

The depot formulation of the present invention have advantageous properties: they have low hemolysis and toxicity potential and show good local tolerability at the injection site in rabbits. Sustained release systems in accordance with the present invention improve patience compliance and life standard. Furthermore the manufacturing process is simple and cheap and no organic solvent is required.

In one preferred embodiment of the present invention, no organic solvent is used during process for preparing the formulation of the present invention and hence no organic solvent is present in the formulation.

The depot formulation of the invention may be stored e.g. in prefilled syringe or other suitable containers, auto-injection device, vial and syringe over an extended period of time without sedimentation at a temperature below the melting point of the solvent such as e.g. the end-capped PEG.

The implant formed after injection into the body may release the active agent over an extended period of time. The desired release profile may depend on the kind of monomer, whether a homo- or a co-polymer or whether a mixture of polymers is employed. The release period may range from 1 up to 12 weeks, e.g. 1 to 8 weeks such as e.g. 4 weeks.

Optionally an additive may be added to the polymer/solvent solution and/or to the polyethylene glycol/drug substance solution. The additive may improve the solubility of the polymer and the drug substance of the active ingredient. The co-solvent may further modulate the drug release in vitro or in vivo. The additive may be present in an amount of about 0.1% to about 20% w/v, preferably from about 1% to about 5%. Examples of such additives include methanol, ethanol, propylene glycol, liquid surfactant such as poly(oxyethylene) sorbitan esters (Tweens) or glycerin polyoxyethylene ester of castor oil (Cremophor EL), lactic acid, acetic acid, glycerol, N,N dimethylacetamide, benzyl benzoate, polyoxyethylated fatty acid, lecithin, soybean oil, seaflower oil, vegetable oils, cotton sead oils, oligormers of poly(l-lactide) of poly(d,l lactide) of poly(lactide co-glycolide) or a mixture of these oligomers.

Details of suitable excipients for use in the compositions or process of the invention are described e.g. in the "Handbook of Pharmaceutical Excipients", Rowe, Sheskey and Weller, $4^{th}$ Edition 2003.

In a further aspect of the invention the composition obtainable by the process of the present invention may be in liquid form at room temperature, e.g. a solution. After sterile filtration through a 0.22 micrometer filter the liquid composition, e.g. solution, may be placed in a syringe. Sterilization may also be achieved by another terminal sterilization with gamma irradiation at 20 to 30 kGy preferably at 25 kGy under cooled conditions, e.g. 2 to 8° C. or −70° C. The sterilized solution may be injected through a needle, e.g. an up to 20 G needle, into the body subcutaneously or intramuscularly. Once in place the solvent, e.g. polyethylene glycol will dissipate and the polymer together with the pharmaceutically active agent solidifies to form the implant. Accordingly to the invention, preferably a prefilled syringe may be provided together with instructions for use.

The compositions of the invention are useful for treatment of the known indications of the particular active agent incorporated in the polymer in the indications as described on page 11 of WO02/010192. Preferably, the compositions of the invention are useful in the treatment of acromegaly and cancer, e.g. carcinoid tumor, Cushing's Disease.

The activity and the characteristics of the liquid compositions of the invention may be indicated in standard clinical or animal tests. Appropriate dosage of the composition of the invention will of course vary, e.g. depending on the condition to be treated (for example the disease type of the nature of resistance), the drug used, the effect desired and the mode of administration.

For compositions of the invention comprising a somatostatin analogue satisfactory results are obtained on administration, e.g. parenteral administration, at dosages on the order of from about 0.2 to about 60 mg, preferably from about 5 to about 40 mg per injection per month or about 0.03 to about 1.2 mg per kg animal body weight per month, administered once or in divided doses. Suitable monthly dosages for patients are thus in the order of about 0.3 mg to about 40 mg of a somatostatin analogue, e.g. Compound a pamoate. The composition may be administered every 2 to 3 months. Suitable dosages for every 3 months administration are about 1 mg to about 180 mg.

It has been found in accordance with the present invention that PEG500 DME has particularly advantageous properties as solvent for parenteral formulations, e.g. a low hemolytic potential, a viscosity suitable for injection, stability of PLGA solutions in PEG500DME, a favorable correlation between phase separation and the in vitro release and a low initial burst. Thus, in another aspect of the present invention, PEG500 DME is provided as solvent in a pharmaceutical composition for parenteral use, e.g. for an active substance described above or in the Examples below.

In one embodiment the present invention provides a pharmaceutical composition for injection comprising an active substance and PEG500 DME as co-solvent. Such composition may contain from 10% to 99.5%, 20% to 90%, 30% to 80% or 50% to 99.5% (total weight of the composition); or 50% to 100% or 60% to 99% of PEG500 DME e.g. in an aqueous solution.

Following is a description by way of example only of processes and compositions of the invention.

To outline the suitability of PEG500DME as a solvent for parenteral use, a hemolysis study was performed:

TABLE 1

Hemolysis in [%] of solvents (PEG500 DME, PEG 600 and NMP) tested in a female donor and a male donor. Table 1 summarizes values for the hemolytic activity of 3 solvents. PEG 500 shows lower hemolysis values of the pure solvent compared to PEG600 and NMP; NMP in a concentration of 1:2 still shows hemolytic activity compared to PEG 500 DME and PEG 600.

Hemolysis [%] in female/male donor

| solvent | Dilutions with 0.9% NaCl solution | | | | | | | |
|---|---|---|---|---|---|---|---|---|
| | 0 | 1:2 | 1:4 | 1:8 | 1:16 | 1:32 | 1:64 | 1:128 |
| PEG 600 | 13/8 | 1/0 | 0/0 | 1/0 | 1/0 | 1/0 | 1/0 | 1/0 |
| NMP | 54/28 | 10/0 | 1/0 | 1/0 | 1/0 | 1/0 | 1/0 | 1/0 |
| PEG 500 DME | 2/6 | 0/0 | 0/0 | 1/0 | 1/0 | 1/0 | 1/0 | 1/0 |

TABLE 2

Hemolysis [%] of the three investigated solvents, tested in erythrocytes of female and male blood donor (n = 4). 48.8% erythrocytes showed lysis using undiluted NMP. At a dilution of 1:2 with isotonic NaCl solution, NMP still shows 7.8% hemolysis. 13.3% hemolysis was observed for undiluted PEG600. For a dilution of PEG600 with isotonic NaCl solution (1:2), 2.0% hemolysis was determined. The lowest hemolytic activity of all undiluted solvents was represented by PEG500DME with 5.5%. No significant hemolytic effects were shown for further dilutions of the three solvents.

Hemolysis [%]

| solvent | Dilutions with 0.9% NaCl solution | | | | | | | |
|---|---|---|---|---|---|---|---|---|
| | 0 | 1:2 | 1:4 | 1:8 | 1:16 | 1:32 | 1:64 | 1:128 |
| NMP | 48.8 ± 21.1 | 7.8 ± 5.6 | 0.5 ± 0.6 | 0.3 ± 0.5 | 0.3 ± 0.5 | 0.3 ± 0.5 | 0.3 ± 0.5 | 0.3 ± 0.5 |
| PEG600 | 13.3 ± 3.8 | 2.0 ± 1.8 | 0 | 0 | 0 | 0 | 0 | 0 |
| PEG500DME | 5.5 ± 4.7 | 0 | 0 | 0.3 ± 0.5 | 0.3 ± 0.5 | 0.3 ± 0.5 | 0.3 ± 0.5 | 0.3 ± 0.5 |

FIG. 1 demonstrates the in-vitro release of a 5% (drug substance base) loaded suspension with SOM230 over 48 days.

FIG. 2 presents the in-vitro release profile of a 3.5% (drug substance base) loaded suspension with SOM230 over 48 days.

Figure 6:
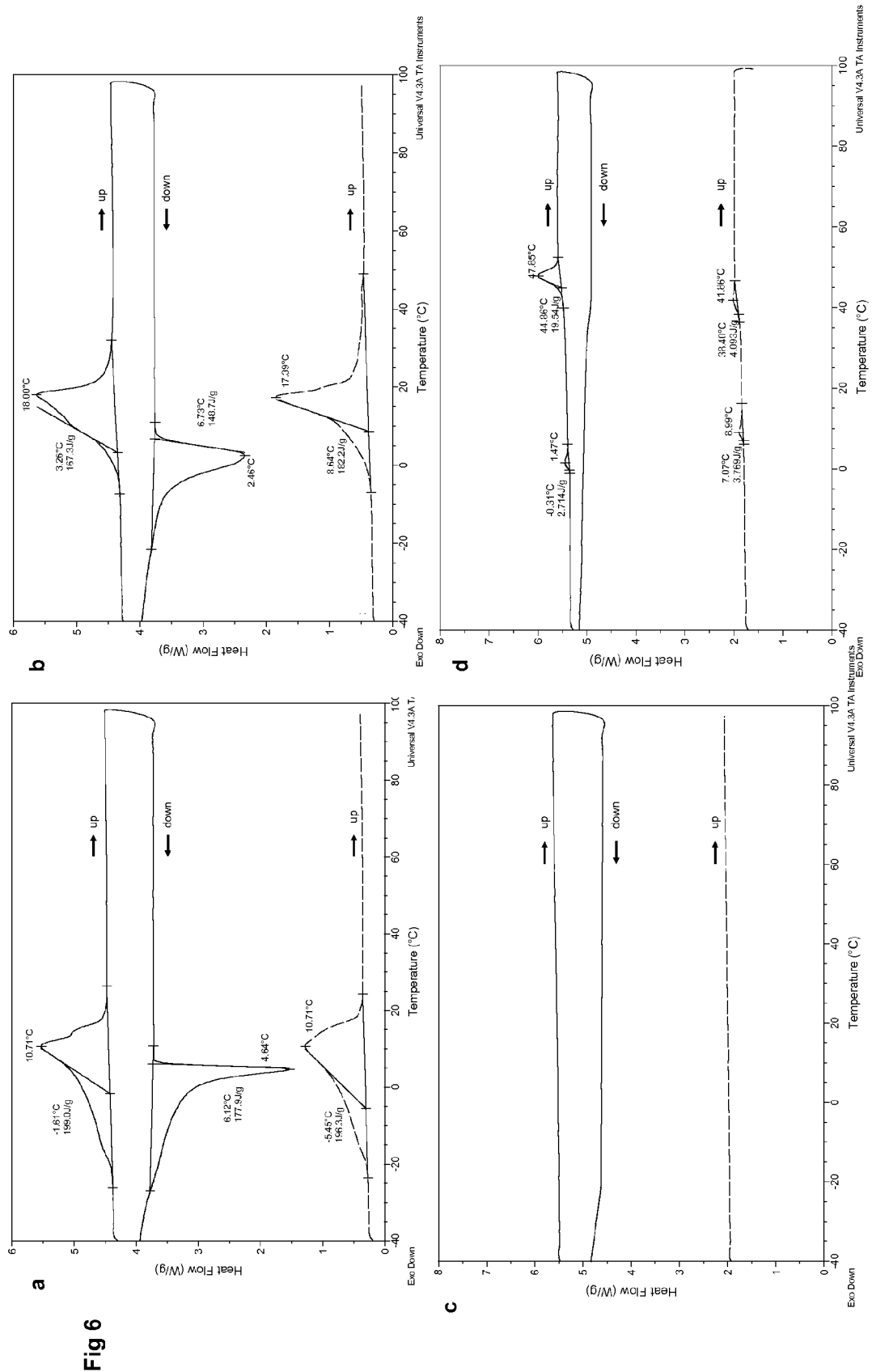

FIG. 6 shows DSC thermograms for PEG500DME (6a); PEG600 (6b); NMP (6c); and pure PLA50GA5012 (6d).

Figure 7:
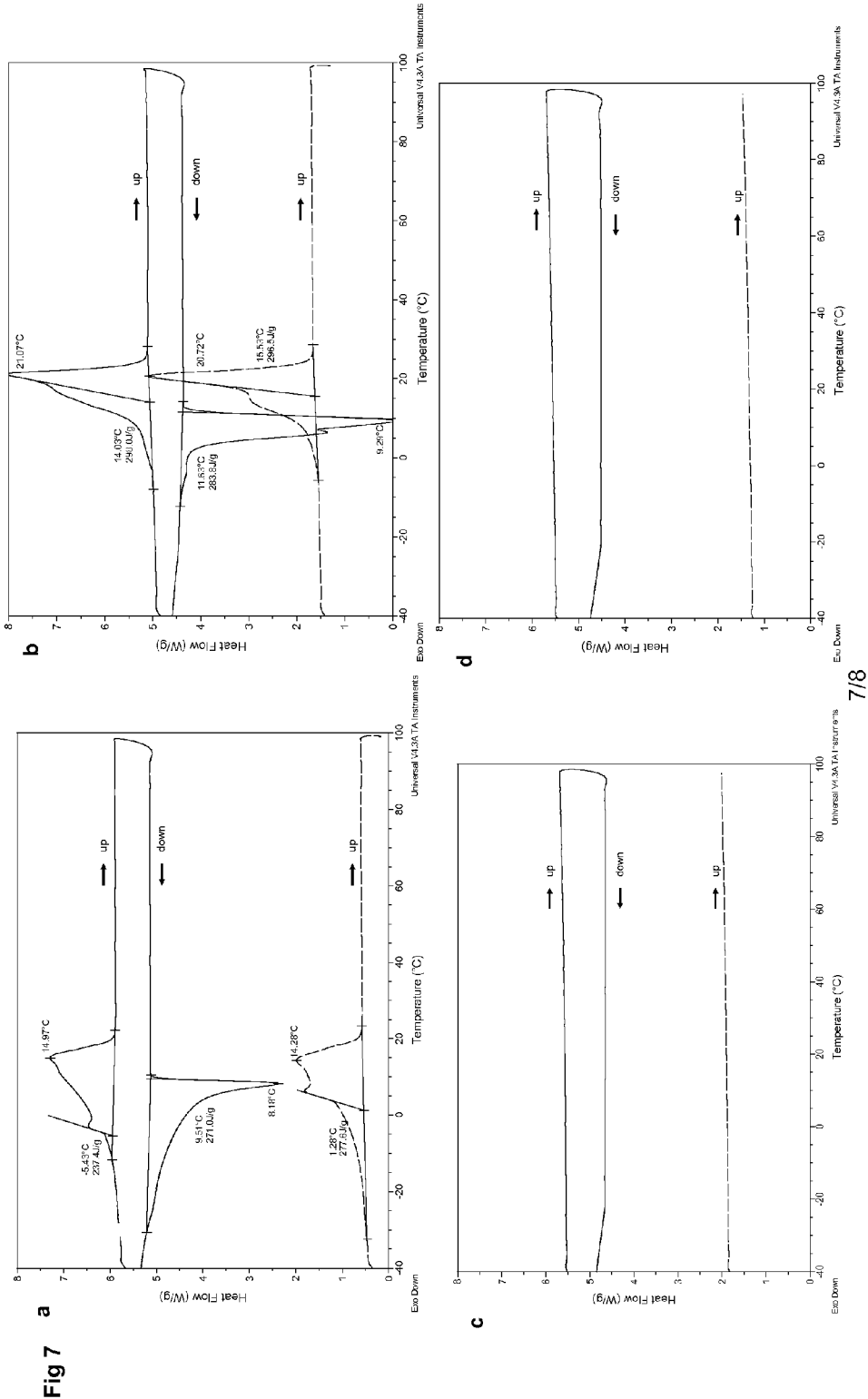

FIG. 7 shows t DSC thermograms for the solution of 20% (w/w) PLA5oGA5o12 in PEG500DME as compared to the pure solvent (7a); a solution of 20% PLA50GA5012 in PEG600 (7b); and the solutions of 20% and 40% PLA50GA5012 in NMP (7c and 7d, respectively).

Figure 8:
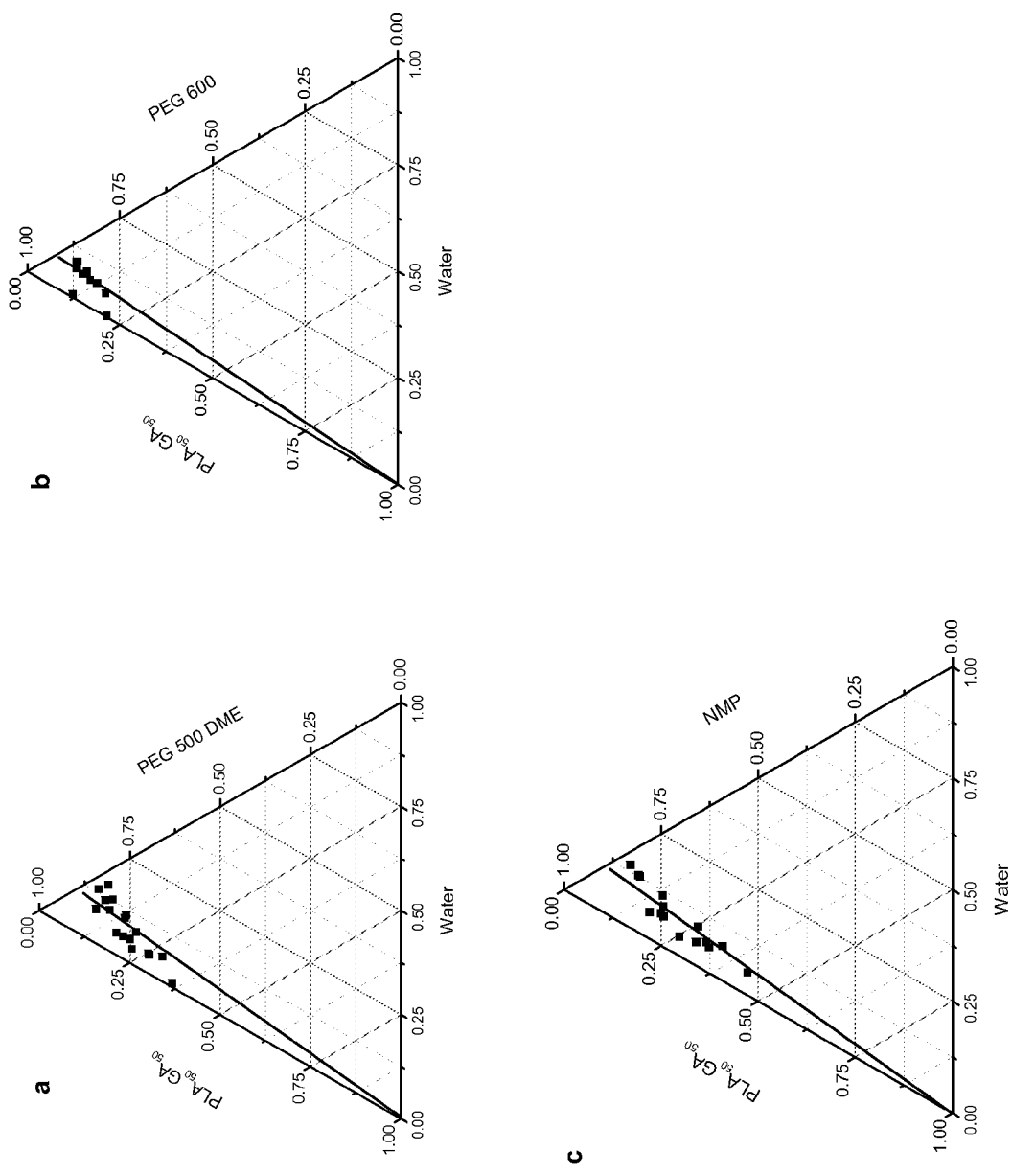

FIG. 8 shows ternary phase diagrams for PLA50GAso12 solutions in PEG500DME (8a); PEG600 (8b); and NMP (8c).

EXAMPLE 1

Figure 1:
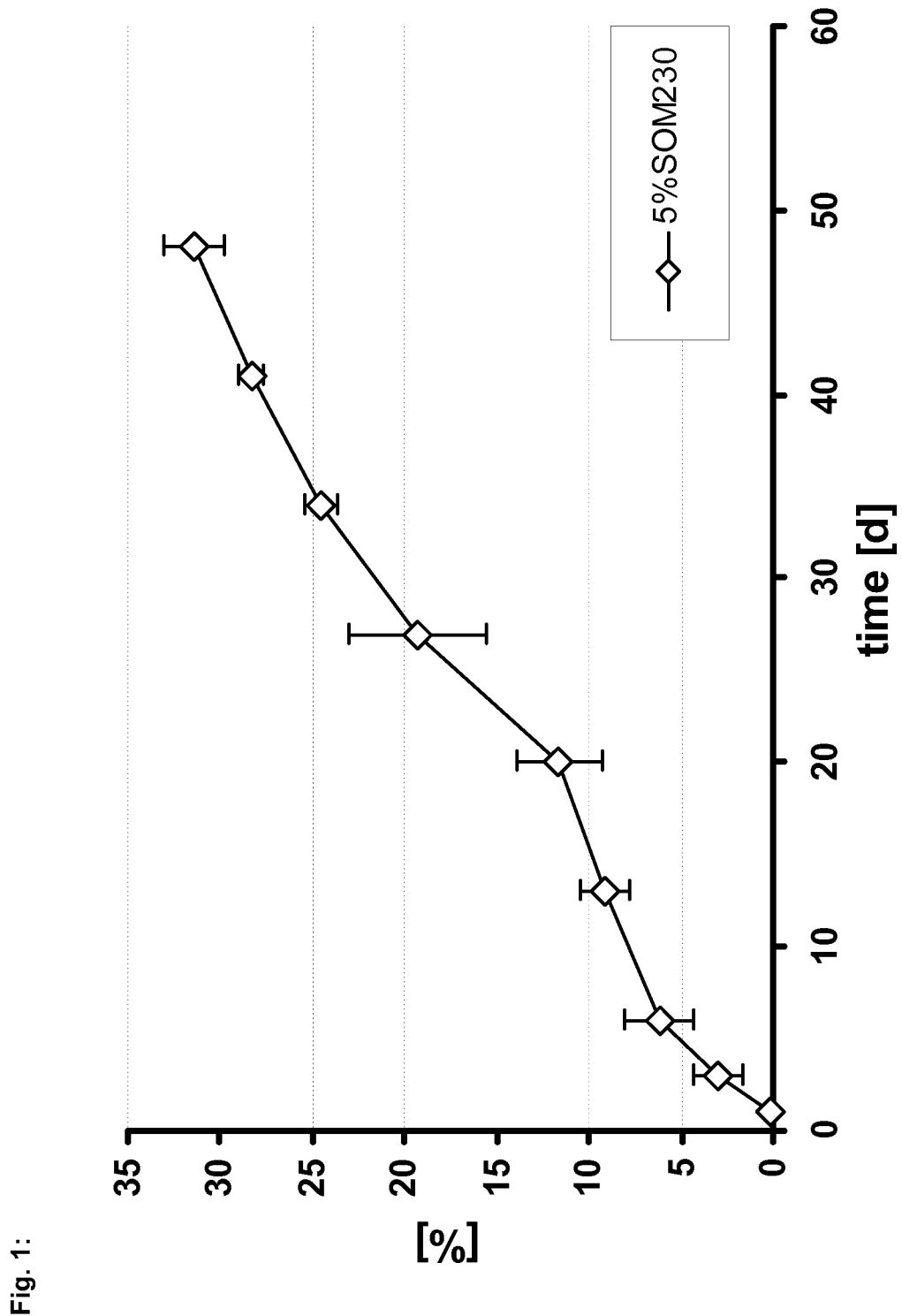

0.960 g Poly (D,L-lactide-co-glycolide) 50:50 (20% w/w) is dissolved in 3.5062 g Poly (ethylene glycol) 500 dimethylether. 0.3404 g gamma irradiated pharmaceutically active agent SOM230 pamoate (=0.250 g tree base=5% w/w) is added to the polymer solution after sterile filtration (Millex GV, 0.22 micrometer, Millipore, Zug, Switzerland) with 1 bar N2 pressure and dispersed in the solution by magnetic stirring. The dispersion is sonicated 2*5 min with an ultrasound probe (hielscher UP400S, Ultrasound technology, Stuttgart, Germany) to a mean particle size of approx. 51 micrometer (determined with a Lasentec probe, Mettler-Toledo, Greifensee, Switzerland). 0.240 g formulation (+overfill=0.333 g) are filled in 1 ml syringes (BD, 1 ml syringe with Luer-Lok tip, Franklin Lakes, N.J., USA) with a 22G needle (Sterican, 0.70×0.30 BL/LB, B. Braun, Melsungen, Germany). The amount of injected formulation is adjusted to approx. 0.012 g drug substance base. The in situ depot formulation is injected directly in 12 mm cells (diameter) filled with 2 ml PBS buffer pH 7.4 and placed in a USP 4 apparatus (Sotax, Allschwil, Switzerland) for in-vitro release. Buffer pH 7.4 is pumped through the apparatus with an Ismatec IP pump (Ismatec, Glattbrugg, Switzerland) at flow rate of 0.5 ml/h. Samples are collected after 1, 3, 6, 13, 20, 27, 34, 41, 48 days and analyzed by HPLC. FIG. 1 shows a sustained in-vitro release profile over 48 days of approx. 30% of the theoretical drug content with very low initial release (burst).

EXAMPLE 2

Figure 2:
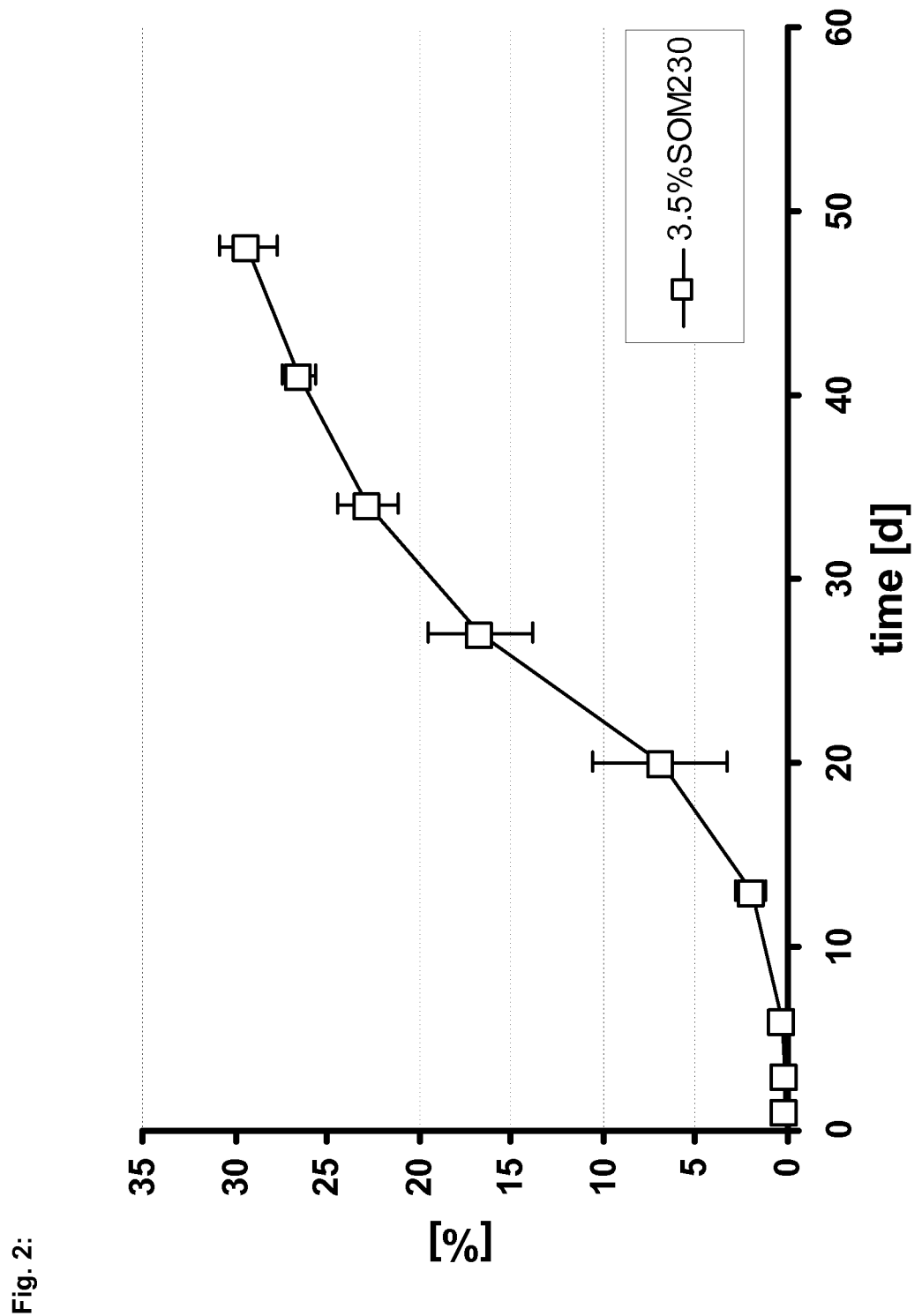
Figure 3:
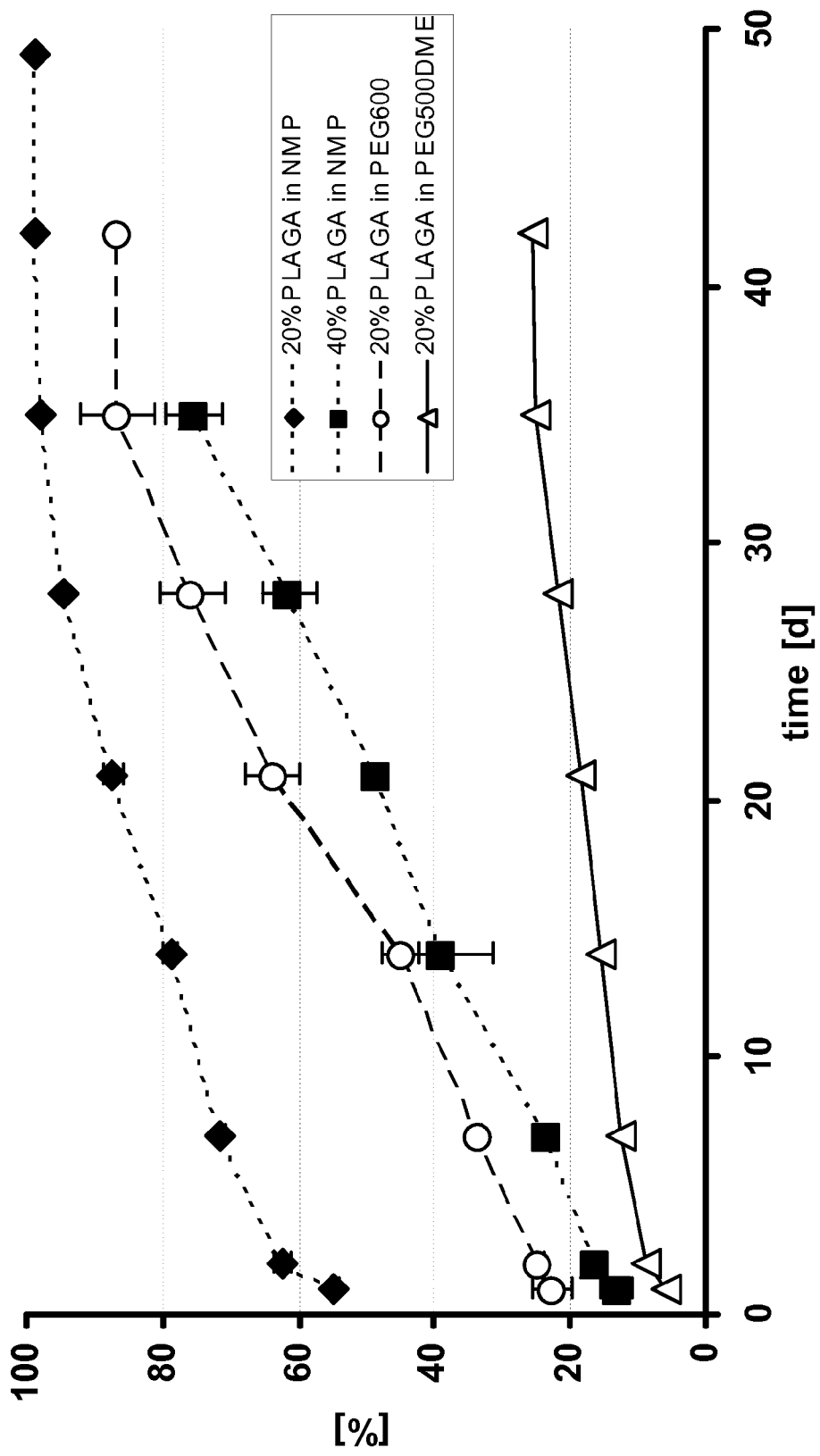
FIG. 3 shows the release of methylene blue out of 4 formulations injected with a 1 ml syringe and a 23G needle, where a 20% PLGA50:50 solution in PEG500DME indicates a very low burst and, constant sustained release over the observation time of 49 days.
Figure 4:
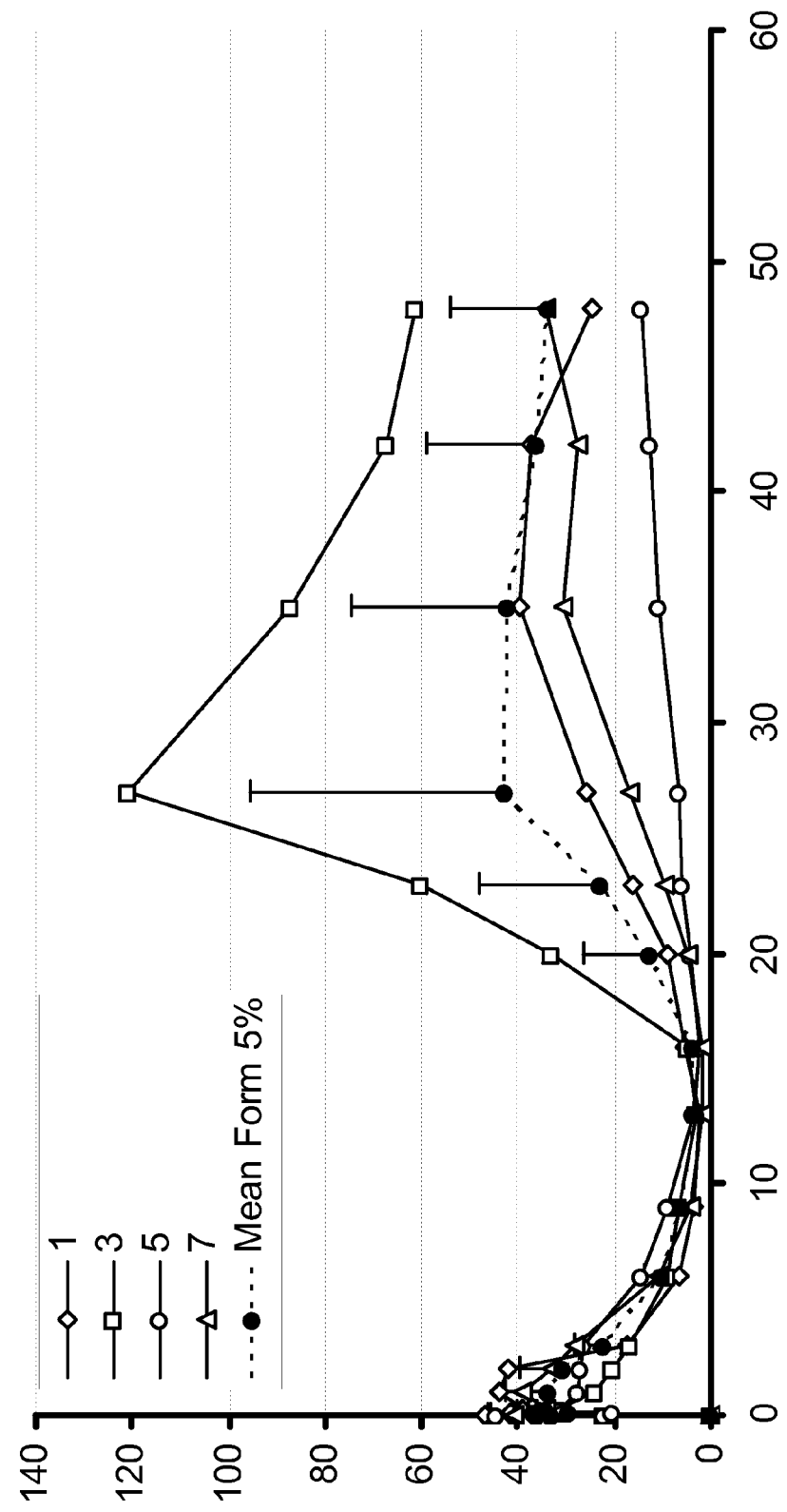
FIG. 4 represents the in-vivo release of a 5% (drug substance base) loaded suspension with SOM230 over 48 days in rabbits.
Figure 5:
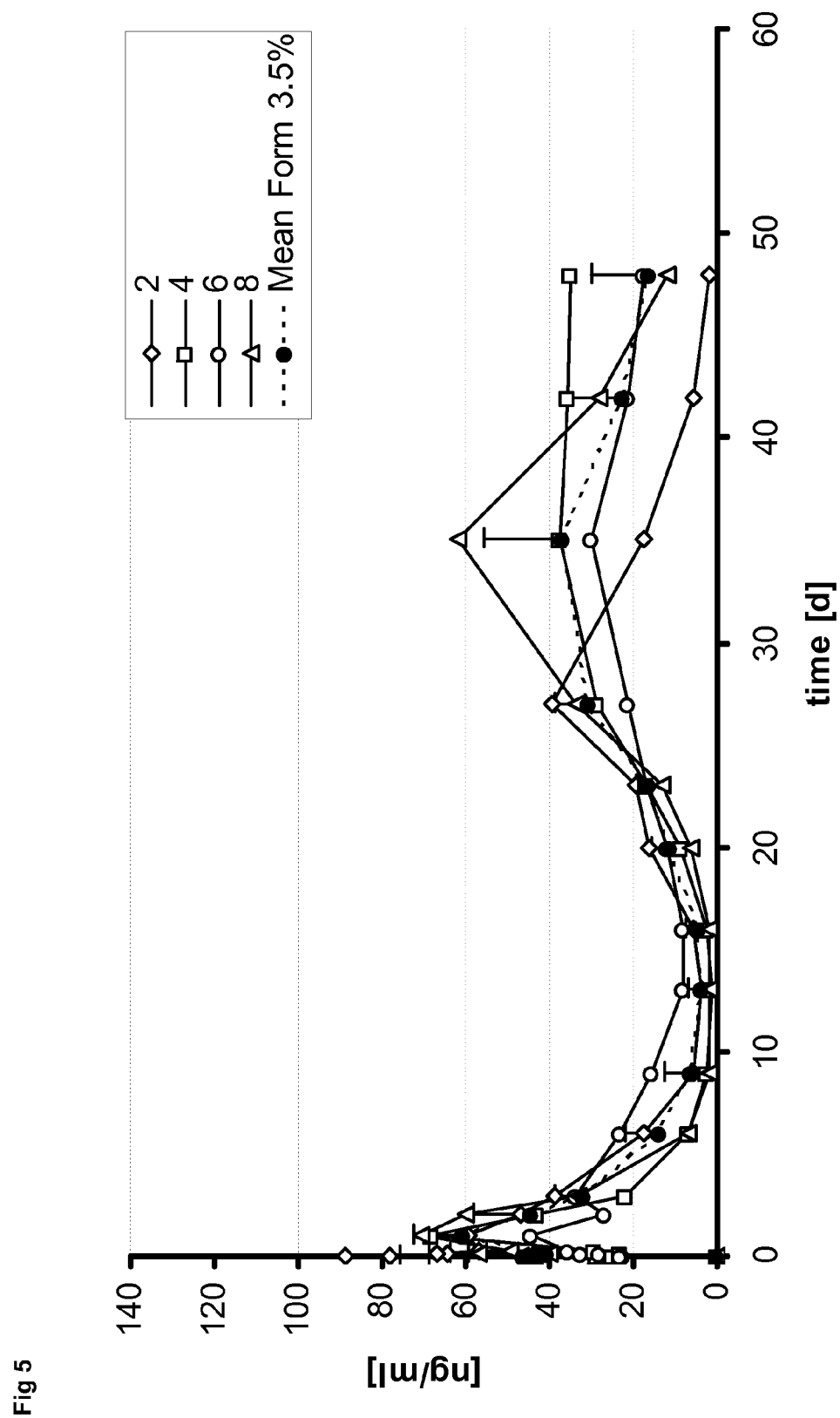
FIG. 5 shows the in-vivo release profile in rabbits of a 3.5% (drug substance base) loaded suspension with SOM230 over 48 days.

1.00139 g Poly (D,L-lactide-co-glycolide) 50:50 (20% w/w) are dissolved in 3.75521 g Poly (ethylene glycol) dimethylether. 0.2523 g gamma irradiated pharmaceutically active agent SOM 230 pamoate (=0.180 g free base=3.5% w/w) is added to the polymer solution after sterile filtration (Millex GV, 0.22 micrometer, Millipore, Zug, Switzerland) with 1 bar N2 pressure and dispersed in the solution by magnetic stirring. The dispersion is sonicated 2*5 min with an ultrasound probe (hielscher UP400S, Ultrasound technology, Stuttgart, Germany) to a mean particle size of approx. 54 micrometer (determined with a Lasentec probe, Mettler-Toledo, Greifensee, Switzerland). 0.3301 g formulation (+overfill=0.420 g) are filled in 1 ml syringes (BD, 1 ml syringe with Luer-Lok tip, Franklin Lakes, N.J., USA) with a 22G needle (Sterican, 0.70×0.30 BL/LB, B. Braun, Melsungen, Germany). The amount of injected formulation is adjusted to approx. 0.012 g drug substance base. The in situ depot formulation is injected directly in 12 mm cells (diameter) filled with 2 ml PBS buffer pH 7.4 and placed in a USP 4 apparatus (Sotax, Allschwil, Switzerland) for in-vitro release. Buffer pH 7.4 is pumped through the apparatus with an Ismatec IP pump at flow rate of 0.5 ml/h. Samples are collected after 1, 3, 6, 13, 20, 27, 34, 41, 48 days and analyzed by HPLC. FIG. 2 shows a sustained in-vitro release profile over 48 days of approx. 30% of the theoretical drug content with very low initial release (burst).

EXAMPLE 3

0.048 g pharmaceutically active agent (0.6% methylene blue) is added to 4 polymer solutions with different solvents. The first solution comprises 1.6002 g Poly (D,L-lactide-co-glycolide) 50:50 (20% w/w) and 6.4345 g Poly (ethylene glycol) 500 dimethylether, the second solution includes 1.6004 Poly (D,L-lactide-co-glycolide) 50:50 (20% w/w) dissolved 6.4092 g N-Methylpyrrolidine, the third solution of 3.2006 g Poly (D,L-lactide-co-glycolide) 50:50 (40% w/w) in 4.818 g N-Methylpyrrolidine and the last solution of 1.6012 g Poly (D,L-lactide-co-glycolide) 50:50 (20% w/w) in Poly (ethylene glycol) 600.

0.400-0.500 g of methylene blue loaded polymer solutions are injected (1 ml syringe (BD 1 ml with Luer-Lok tip, BD, Franklin Lakes, N.J., USA) and a 23G needle (BD Microlance 3.0.6×25 mm, BD, S.A. Fraga, Spain) into 50 ml polypropylene Falcon tubes (BD, Franklin Lakes, USA) with 25 ml PBS buffer pH 7.4. The tubes are incubated in a water shaker bath (A D Krauth, Hamburg, Germany) at 37° C. at very low frequency. Buffer replacement is performed at every sampling point. The samples are taken at t=0, 1, 3, 7, 14, 21, 28, 35, 42 and 49 days and analyzed with a Varian Cary spectrophotometer (Darmstadt, Germany) at a wavelength of 665 nm.

EXAMPLE 4

0.960 g Poly (D,L-lactide-co-glycolide) 50:50 (20% w/w) is dissolved in 3.5062 g Poly (ethylene glycol) 500 dimethylether. 0.3404 g gamma irradiated pharmaceutically active agent SOM230 pamoate (=0.250 g free base=5% w/w) is added to the polymer solution after sterile filtration (Miliex GV, 0.22 micrometer, Millipore, Zug, Switzerland) with 1 bar N2 pressure and dispersed in the solution by magnetic stirring. The dispersion is sonicated 2*5 min with an ultrasound probe (hielscher UP400S, Ultrasound technology, Stuttgart, Germany) to a mean particle size of approx. 51 micrometer (determined with a Lasentec probe, Mettler-Toledo, Greifensee, Switzerland). 0.240 g formulation (+overfill=0.333 g) are filled in 1 ml syringes (BD, 1 ml syringe with Luer-Lok tip, Franklin Lakes, N.J., USA) with a 22G needle (Sterican, 0.70×0.30 BULB, B. Braun, Melsungen, Germany). The amount of injected formulation is adjusted to approx. 0.012 g drug substance base per animal. Four rabbits are tested on the in-vivo drug release of SOM230 pamoate. The in situ depot formulation is injected subcutaneously in the neck area of each rabbit. Blood samples (1-1.5 mL) were collected from *V. auricularis* into polypropylene syringes containing 1.6 mg potassium-EDTA (S-Monovette, Sarstedt AG, Sevelen, Switzerland). The samples were taken after 0 (=pre-dose), 30 min, 1, 2, 4, 6 hours, 1, 2, 3, 6, 9, 13, 16, 20, 23, 27, 35, 42 and 48 days. The plasma samples were analyzed for SOM230 using a competitive ELISA test.

EXAMPLE 5

1.00139 g Poly (D,L-lactide-co-glycolide) 50:50 (20% w/w) are dissolved in 3.75521 g Poly (ethylene glycol) 500 dimethylether. 0.2523 g gamma irradiated pharmaceutically active agent SOM230 pamoate (=0.250 g free base=2.5% w/w) is added to the polymer solution after sterile filtration (Millex GV, 0.22 micrometer, Millipore, Zug, Switzerland) with 1 bar N2 pressure and dispersed in the solution by magnetic stirring. The dispersion is sonicated 2*5 min with an ultrasound probe (hielscher UP400S, Ultrasound technology, Stuttgard, Germany) to a mean particle size of approx. 54 micrometer (determined with a Lasentec probe, Mettler-Toledo, Greifensee, Switzerland). 0.3301 g formulation (+overfill=0.420 g) are filled in 1 ml syringes (BD, 1 ml syringe with Luer-Lok tip, Franklin Lakes, N.J., USA) with a 22G needle (Sterican, 0.70×0.30 BL/LB, B. Braun, Melsungen, Germany). The amount of injected formulation is adjusted to approx. 0.012 g drug substance base per animal. Four rabbits are tested on the in-vivo drug release of SOM230 pamoate. The in situ depot formulation is injected subcutaneously in the neck area of each rabbit. Blood samples (1-1.5 mL) were collected from *V. auricularis* into polypropylene syringes containing 1.6 mg potassium-EDTA (S-Monovette, Sarstedt AG, Sevelen, Switzerland). The samples were taken after 0 (=pre-dose), 30 min, 1, 2, 4, 6 hours, 1, 2, 3, 6, 9, 13, 16, 20, 23, 27, 35, 42 and 48 days. The plasma samples were analyzed for SOM230 using a competitive ELISA test.

EXAMPLE 6

0.5 g Cyclosporine A was dissolved in 9.5 g Poly (ethylene glycol) 500 dimethylether by magnetic stirring. A clear solution was obtained within 3 h.

EXAMPLE 7

PEG500DME, PEG600 and solutions of 20% (w/w) $PLA_{50}GA_{50}12$ in the two PEGs were tempered at −40° C. for 0.5, 4 and 8 h after the first DSC heating and cooling cycle. No difference in the melting behavior was observed for the solvents and the polymer solutions during the second heating cycle (data not shown). The crystalline structure of the pure PEGS seemed to be independent of the tempering interval. No change in the melting behavior was found for the polymer solutions due to the tempering duration. This was an important finding with regard to the long term stability of the $PLA_{50}GA_{50}12$ solutions, because they seemed to be able to maintain their properties throughout the cooling procedure.

The melting points for PEG500DME were 14.7±0.4° C. and 21.8±0.7° C. for PEG600 (FIGS. 6a and b) as determined by DSC. In both thermograms, broad signals for the melting peak in the first heating cycle and a broad signal for the exothermal crystallization during the cooling cycle appeared. The thermal observation of NMP in the same temperature range did not show any first order transitions (FIG. 6c). The thermogram for pure $PLA_{50}GA_{50}12$ is shown in FIG. 6d. A small endothermal peak, most probably of water, was observed at 0.31° C. in the first heating cycle. The endothermal relaxation of the polymer powder was visible, with an endothermal peak at 47.9° C. No aging was observed during the subsequent cooling cycle. In the second heating cycle, the glass transition temperature ($T_g$) was identified at 39.5±2.6° C.

A melting point depression was observed for the solution of 20% (w/w) $PLA_{50}GA_{50}12$ in PEG500DME to 10.9±0.4° C. (FIG. 7a) as compared to the pure solvent. In the first heating cycle, gradual melting was visible, and this resulted in a broad peak with several shoulders. During the cooling cycle, the onset of crystallization was at 5.8±0.5° C., as noticed with a tailing of the peak. A broad melting peak was again observed during the second heating cycle after 0.5 h tempering at −40° C. No signal for the $T_g$ of $PLA_{50}GA_{50}12$ was detected in the second heating cycle. For a solution of 20% $PLA_{50}GA_{50}12$ in PEG600, again a significant decrease of the melting temperature to 18.4±0.6° C. was observed (FIG. 7b). A broad melting peak with two stages in the first heating cycle was visible in the thermogram. The crystallization peak during cooling and the second heating cycle at 3.7±0.8° C. showed broad signals. For the solutions of 20% and 40% $PLA_{50}GA_{50}12$ in NMP, no signal for melting, crystallization or $T_g$ was detected in the observed temperature range. (FIGS. 7c and d).

EXAMPLE 8

$PLA_{50}GA_{50}12$ solutions in NMP, PEG500DME and PEG600 at different concentrations were investigated for the onset of polymer precipitation in presence of water at 37° C. (FIG. 8). The straight line in the diagrams was drawn from 100% $PLA_{50}GA_{50}12$ and divided the area into the upper homogenous three component system and a binary system (Phase separation) below the line. The onset of polymer precipitation was determined for different $PLA_{50}GA_{50}12$ concentrations in PEG500DME by addition of solvent/water mixtures to solutions of polymer in organic solvent. Polymer precipitation already occurred in presence of 1.0% water for a solution of 32.6% $PLA_{50}GA_{50}12$ in PEG500DME (FIG. 8a), signifying that only a small amount of water was necessary to precipitate the hydrophobic polymer in the solution. 13.4% water was required to precipitate the polymer out of 3.0% $PLA_{50}GA_{50}12$ in PEG500DME. As expected, the addition of an increased quantity of water at lower polymer content was possible (7).

The ternary phase diagram using PEG600 (FIG. 8b) as solvent reveals that only 0.3% uptake of water is needed to precipitate the polymer at a content of 24.8%. At a low $PLA_{50}GA_{50}12$ content (3.5%), 9.2% water had to be added to induce the onset of turbidity in the polymer solution. The $PLA_{50}GA_{50}12$ solutions in PEG600 acted similarly to the solutions in PEG500DME, displaying precipitation at increased polymer and low water content. Accordingly, an increased tolerability of water until precipitation was observed at low polymer concentrations.

The ternary phase diagram of $PLA_{50}GA_{50}12$ in NMP (FIG. 8c) shows a miscible homogenous system up to 50% polymer in 50% solvent (w/w). At a water content of 4.7%, turbidity appeared in a solution of 45.6% $PLA_{50}GA_{50}12$ in 49.6% NMP. The capacity to dissolve $PLA_{50}GA_{50}12$ was significantly increased in NMP relative to PEG500DME and PEG600. 14.1% water had to be added to 2.9% $PLA_{50}GA_{50}12$ in NMP for precipitation to occur. The area of a miscible homogenous mixture above the straight line was increased in the ternary phase diagram using NMP as solvent compared to PEG500DME or PEG600. The capacity to dissolve $PLA_{50}GA_{50}12$ in PEG500DME and PEG600 was lower than in NMP. Overall, the onset of $PLA_{50}GA_{50}12$ precipitation occurred at lower concentrations in PEG500DME and PEG600 compared to NMP.

The invention claimed is:

1. An injectable in situ forming depot formulation comprising
   i) a pharmaceutically active agent, wherein the pharmaceutically active agent is a cyclo [{4-($NH_2$—$C_2H_4$—NH—CO—O—)Pro}-Phg-DTrp-Lys-Tyr(4-Bzl)-Phe] pamoate or di-aspartate,
   ii) a poly (ethylene) glycol with a molecular weight 450<Mw<650Da and with alkoxy end groups which has a solidification point at a temperature between 8° to 20° C.,
   iii) a biodegradable polymer, and optionally
   iv) an additive.

2. An injectable in situ forming depot formulation according to claim 1 wherein the poly(ethylene)glycol is PEG500-DME.

3. An injectable in situ forming depot formulation according to claim 1 wherein the biodegradable polyester is PLA or a linear or branched PLGA.

4. An injectable in situ forming depot formulation according to claim 1 wherein the biodegradable polyester is Polylactide or a Poly (lactide-co-glycolide) with inherent viscosity of 0.15-0.60 dL/g.

5. An injectable in situ forming depot formulation according to claim 1 wherein the formulation is free of organic solvents.

6. A process for preparing an injectable in situ forming depot formulation comprising the steps:
   i) dissolving a biodegradable polyester in a PEG with a molecular weight of at least 450 Da and less than 650 Da and with alkoxy end groups which has a solidification point at a temperature between 8° to 20° C.,
   ii) adding a pharmaceutically active agent, wherein the pharmaceutically active agent is a cyclo [{4-($NH_2$—$C_2H_4$—NH—CO—O—)Pro}-Phg-DTrp-Lys-Tyr(4-Bzl)-Phe] pamoate or di-aspartate, and optionally an additive to achieve a solution or suspension,
   iii) and in case a suspension is obtained milling the formulation by an appropriate particle size reduction process to expected mean particle size.

7. A process for preparing an injectable in situ forming depot formulation comprising the steps:
   v) dissolving a pharmaceutically active agent, wherein the pharmaceutically active agent is a cyclo [{4-($NH_2$—$C_2H_4$—NH—CO—O—)Pro}-Phg-DTrp-Lys-Tyr(4-Bzl)-Phe]pamoate or di-aspartate, in a PEG with a molecular weight of at least 450 Da and less than 650 Da and with alkoxy end groups which has a solidification point at a temperature between 8° to 20° C.,
   vi) adding a biodegradable polyester to achieve a solution or suspension,
   vii) and in case a suspension is obtained milling the formulation by an appropriate particle size reduction process to expected mean particle size.

8. The process according to claim 6 wherein an organic co-solvent is not used.

9. The process according to claim 6 wherein the polyester is PLA or a linear or branched PLGA.

10. The process according to claim 6 wherein the biodegradable polyester has an inherent viscosity of 0.15-0.60 dL/g (0.1% in chloroform at 25° C.).

11. The injectable in situ forming depot formulation according to claim 1 wherein the active agent is released from the injectable in situ forming depot formulation over 1 up to 12 weeks.

12. A prefilled syringe comprising the formulation of claim 1 in combination with instructions for using said prefilled syringe.

13. A pharmaceutical composition comprising the formulation according to claim 1 in combination with a pharmaceutically acceptable excipient.

14. The pharmaceutical composition according to claim 13, wherein the active agent is released from the injectable in situ forming depot formulation over a period of 1 to 12 weeks.

* * * * *